United States Patent [19]
Chen et al.

[11] Patent Number: 6,084,408
[45] Date of Patent: Jul. 4, 2000

[54] METHODS FOR ACQUISITION AND PROCESSING OF NUCLEAR MAGNETIC RESONANCE SIGNALS FOR DETERMINING FLUID PROPERTIES IN PETROLEUM RESERVOIRS HAVING MORE THAN ONE FLUID PHASE

[75] Inventors: Songhua Chen, Katy; Daniel T. Georgi, Houston, both of Tex.

[73] Assignee: Western Atlas International, Inc., Houston, Tex.

[21] Appl. No.: 09/023,310

[22] Filed: Feb. 13, 1998

[51] Int. Cl.$^7$ ...................................................... G01V 3/00
[52] U.S. Cl. ........................... 324/303; 324/300; 335/296
[58] Field of Search .................................. 324/303, 300, 324/307, 309; 335/296, 302

[56] References Cited

U.S. PATENT DOCUMENTS

| | | | |
|---|---|---|---|
| 5,291,137 | 3/1994 | Freedman | 324/303 |
| 5,486,762 | 1/1996 | Freedman et al. | 324/303 |
| 5,498,960 | 3/1996 | Vinegar et al. | 324/303 |
| 5,517,115 | 5/1996 | Prammer | 324/303 |
| 5,557,200 | 9/1996 | Coates | 324/303 |
| 5,698,979 | 12/1997 | Taicher | 324/303 |
| 5,712,566 | 1/1998 | Taicher | 324/303 |

*Primary Examiner*—Christine K. Oda
*Assistant Examiner*—Brij B. Shrivastav
*Attorney, Agent, or Firm*—Richard A. Fagin; Darryl M. Springs

[57] ABSTRACT

A method for determining intrinsic transverse relaxation time of a first mobile phase in a porous medium using nuclear magnetic resonance measurement sequences. The sequences are measured at first and second wait times. At least two different interecho spacing times are used for each wait time. The first and second wait time are selected to provide different magnetization recoveries of the first phase, and are selected to be longer than the longitudinal relaxation time of a second mobile phase. For the measurements made at the first interecho spacing time, components of signals in the measurements corresponding to the first phase are separated from components corresponding to the second mobile phase by determining differences between the signals measured at the first and at the second wait times. The step of separating is performed for each of the interecho spacing times. An apparent transverse relaxation time of the first mobile phase is calculated from the separated components for each one of the interecho spacing times. A relationship of the apparent transverse relaxation time with respect to the interecho spacing time is determined, and the intrinsic relaxation time is calculated from the relationship. Viscosity of the first mobile phase can be determined from the intrinsic relaxation time.

32 Claims, 2 Drawing Sheets

METHODS FOR ACQUISITION AND PROCESSING OF NUCLEAR MAGNETIC RESONANCE SIGNALS FOR DETERMINING FLUID PROPERTIES IN PETROLEUM RESERVOIRS HAVING MORE THAN ONE FLUID PHASE

BACKGROUND OF THE INVENTION

1. Field of the Invention

The invention is related to the field of nuclear magnetic resonance ("NMR") well logging apparatus and methods. More specifically, the invention is related to methods for acquiring and processing NMR signals to determine particular properties of fluid-bearing earth formations penetrated by wellbores.

2. Description of the Related Art

NMR spin-echo measurements are known in the art for determining certain physical parameters of earth formations penetrated by wellbores. U.S. Pat. No. 5,712,566 issued to Taicher et al gives an explanation of the principles of NMR measurement as applied to determining the physical parameters as well as a description of apparatus used to make NMR measurements in wellbores drilled through earth formations.

Physical parameters of particular interest to wellbore operators are the fractional volume of pore spaces in the earth formations ("porosity") and the nature of the fluids contained in the pore spaces. In petroleum bearing earth formations, the pore spaces will typically contain some fractional volume of water and some fractional volume of hydrocarbons. Since hydrocarbons generally have different NMR relaxation properties than water, various NMR relaxometry techniques have been developed to qualitatively determine the nature of the fluids present in certain earth formations.

One method, for example, enables discriminating between gas and oil, and light oil and water. This method includes performing NMR spin-echo experiments using two different "wait times", TW. The wait time is the delay between individual Carr-Purcell-Meiboom-Gill ("CPMG") spin echo measurement sequences. See S. Meiboom et al, Rev. of Sci. Instr. v. 29, p. 6881 (1958). Another technique, described in U.S. Pat. No. 5,498,960 issued to Vinegar et al, uses two different interecho spacing times, TE, for CPMG sequences measured in a gradient magnetic field. The interecho spacing is the time between rephasing radio frequency (RF) energy pulses applied to the logging instrument's antenna to "rephase" precessing nuclei which are the subject of the NMR experiment. The rephasing RF pulses result in the "spin echoes" whose amplitude is measured. Gas, oil and water generally have different self-diffusivities, and these differences will be reflected in differences in the apparent transverse relaxation time $T_2$ calculated for an earth formation between CPMG sequences measured using different values of TE. The technique described in the Vinegar et al '960 patent for discriminating types of fluids in pore spaces of earth formations typically uses two values of TE.

Another physical property of particular interest is the viscosity of any oil which may be present in the pore spaces of the earth formation. In a paper by R. Akkurt et al entitled, "NMR Logging and Natural Gas Reservoirs", 36th annual symposium, Society of Professional Well Log Analysts (1995), a relationship is described between an intrinsic transverse relaxation time, $T_{2int}$, for oil with respect to its viscosity, $\eta$:

$$T_2 = \frac{1.2\, t_k}{298\, \eta^x} \quad (1)$$

where $t_k$ represents the absolute (Kelvin) temperature of the oil and x represents an empirical fit factor, typically about equal to unity. A difficulty in determining oil viscosity using this relationship is that it requires determining the intrinsic transverse relaxation time. For NMR logging instruments which use a gradient static magnetic field, such as the one described in the Taicher et al '566 patent, the transverse relaxation time calculated from spin-echo amplitude measurements is affected by the self-diffusion effect. The apparent $T_2$ calculated from the spin echo amplitudes is related to $T_{2int}$ in the following manner:

$$\frac{1}{T_2} = \frac{1}{T_{2int}} + \frac{1}{T_{2D}} \quad (2)$$

where the self-diffusion effect $T_{2D}$ can be determined by the expression:

$$\frac{1}{T_{2D}} = \frac{\gamma^2 G^2 D\, TE^2}{12} \quad (3)$$

TE is generally selected by the system operator and has a known value. $\gamma$, the gyromagnetic ratio, is unique for each chemical isotope. The magnitude of the static magnetic field in which the CPMG sequences are actually measured is therefore controlled by selection of the frequency of the RF pulses. Since the spatial distribution of the static magnetic field amplitude and gradient magnitude are known, the gradient of the static magnetic field in the NMR excitation volume will also be known for any selected RF excitation frequency. The actual magnetic field gradient within the pore spaces of the earth formation may not be known, however, since the field gradients internal to the pore spaces depend on differences in magnetic susceptibility between the formation solids ("matrix") and the fluid in the pore spaces, as well as the amplitude of the static magnetic field. See for example, U.S. Pat. No. 5,698,979 issued to Taicher et al. Therefore the relationship in equation (3) is typically not useful to correct $T_2$ values for diffusion effect, because the gradient inside the pore spaces is not readily determinable.

As can be inferred from equations (2) and (3), the difference between the apparent $T_2$ from the CPMG sequence measured at one TE and the apparent $T_2$ determined from the CPMG sequence measured at the other TE could provide information related to the diffusion effect, and thereby the viscosity of any oil which may be present in the pore spaces of the earth formations. It has proven difficult to quantify the difference in apparent $T_2$ using acquisition and processing techniques known in the art, however, because the spin echo amplitude signals acquired using both TE values will typically have some partial contribution from any water present in the pore spaces. The spin echo signals are also typically affected by some amount of noise.

SUMMARY OF THE INVENTION

The invention is a method for determining the intrinsic transverse relaxation time of a first mobile phase in the pore spaces of a porous medium by using nuclear magnetic resonance spin echo amplitude measurements. The measurements are made in CPMG sequences using first and second wait times between sequences. At least two different interecho spacing times are used in the sequences measured using each wait time. The first and second wait times are selected to provide different longitudinal relaxation of the first phase between sequences. For the measurements made at a first interecho spacing time, signal components of the echo amplitude measurements corresponding to the first phase are separated from signal components corresponding to a second mobile phase by determining differences between the echo amplitudes measured at the first and at the second wait times. The second phase has a longitudinal relaxation time shorter than both the first and second wait times, so that the differences between spin echo amplitudes at the first and second wait times substantially exclude any contribution from the second phase. The step of separating is repeated for the CPMG sequences measured using each of the other interecho spacing times.

An apparent transverse relaxation time of the first mobile phase is calculated from the separated first phase signal components, for sequences measured using each one of the interecho spacing times. A relationship of the apparent transverse relaxation time with respect to the interecho spacing time is determined, and the intrinsic relaxation time is determined from the relationship. In one embodiment of the invention, the apparent transverse relaxation time can be determined by inversion processing the separated signal components.

In a particular embodiment, the viscosity of the first mobile phase can be determined from the intrinsic transverse relaxation time this calculated.

In another embodiment of the invention, a longitudinal relaxation time of the first phase can be determined by measuring nuclear magnetic resonance spin echo amplitudes at a first wait time and at a second wait time between CPMG measurement sequences. The first and second wait times are selected to provide different longitudinal relaxation of the first phase. In a particular embodiment, the first wait time is longer than a longitudinal relaxation time of the first phase. The first and said second wait times are both longer than a longitudinal relaxation time of a second mobile phase in the porous medium. A transverse relaxation time distribution of the medium is determined by inverting the spin echo amplitudes measured using the first wait time. Magnitudes of components are determined at values of transverse relaxation times corresponding to known values of transverse relaxation times for the first mobile phase. Components of the first mobile phase in the amplitude signals are then separated from the spin echo amplitudes by determining differences between the spin echo amplitudes measured using the first and second wait times. The longitudinal relaxation time of the first mobile phase is then determined by comparing the component magnitudes from the inversion process to the separated components determined from differences between amplitudes measured at the two different wait times. The viscosity of the first phase can be determined from the longitudinal relaxation time.

DESCRIPTION OF THE PREFERRED EMBODIMENT

Figure 1:
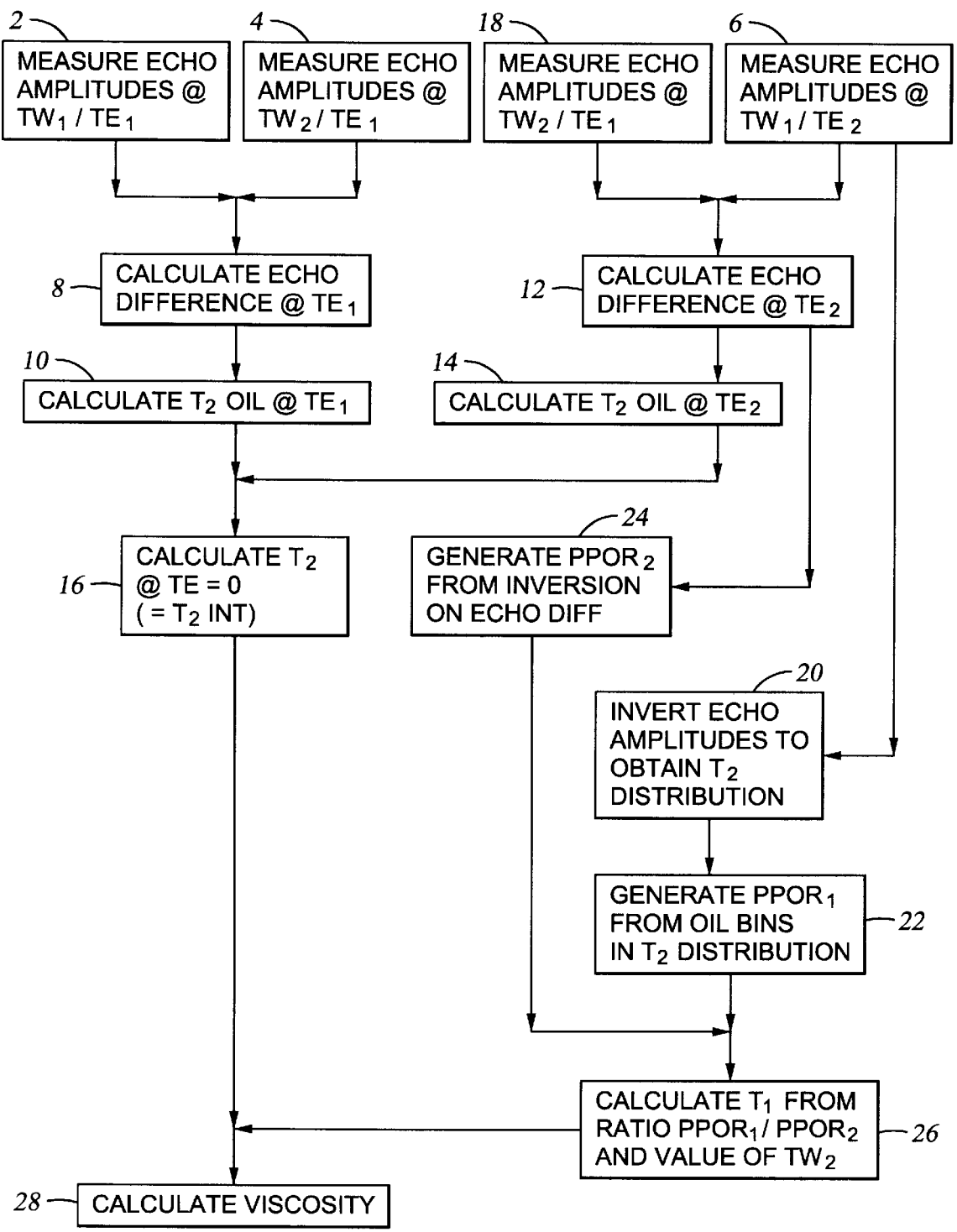
FIG. 1 shows a flow chart of the method of the invention.

A well logging instrument suitable for acquiring nuclear magnetic resonance ("NMR") spin-echo amplitude signals to be used with this invention is described, for example in U.S. Pat. No. 5,712,566 issued to Taicher et al. Described very generally, a permanent magnet on the well logging instrument polarizes nuclei in earth formations surrounding a wellbore into which the logging instrument is inserted. The nuclei are polarized along the direction of the static magnetic field induced by the permanent magnet. Pulses of radio-frequency (RF) energy are passed through an antenna on the instrument causing the nuclei in the formation to be momentarily reoriented along a radio frequency magnetic field induced by the RF energy passing through the antenna. Voltages are induced in the antenna which correspond to precession of axes of rotation of the nuclei about the RF and static magnetic fields. The logging instrument described in the Taicher et al '566 patent can be operated to make Carr-Purcell-Meiboom-Gill (CPMG) spin echo amplitude measurement sequences. The instrument disclosed by Taicher et al can make CPMG sequences having selected wait times (the delay between CPMG sequences), TW, and selected inter-echo spacings (the time between RF rephasing pulses), TE. More typically, the NMR well logging instruments known in the art, including the one disclosed by Taicher et al, make measurements using pairs of opposed-polarity CPMG sequences known as "phase alternate pairs" ("PAPS"), to reduce the effects of antenna "ringing" on the measured spin echo amplitudes. Using PAPS measurement sequences is not a limitation on the invention.

Measurements of spin-echo amplitude from the CPMG (or PAPS) sequences can be used to calculate various petrophysical parameters of interest of the formations. See for example, M. N. Miller et al, "Spin Echo Magnetic Resonance Logging: Porosity and Free Fluid Index Determination", paper no. 20561, Society of Petroleum Engineers, Richardson, Tex. (1990), or U.S. Pat. No. 5,517, 115 issued to Prammer et al. Calculating the petrophysical parameters typically includes a process known as "inversion", where a presentation referred to as a $T_2$ spectrum, or $T_2$ distribution, is generated from the spin echo amplitude measurements. The $T_2$ distribution represents the relative (fractional) contribution to the overall spin-echo amplitudes in each CPMG sequence of various components in the formation. Each of the various components can have its own unique transverse relaxation time, $T_2$. Various physical components, such as fluids in the pore spaces of the formation, can have unique transverse relaxation times or combinations of transverse relaxation times each with its own fractional contribution.

1. Determining the Intrinsic Transverse Relaxation Time for Oil, and Determining Oil Viscosity Generally speaking, the $T_2$ values of typical crude oils in pore spaces of earth formations are greater than those of water. A method is known in the art to separate the fractional contribution caused by water from the fractional contribution caused by oil to the spin echo amplitudes in a CPMG measurement sequence. See Akkurt and Prammer, "Selection of Optimal Acquisition Parameters for MRIL Logs", paper TT, 37th annual symposium, Society of Professional Well Log Analysts (1997). The method described by Akkurt and Prammer includes measuring CPMG sequences at two different wait times TW between individual CPMG sequences. During the wait time, the nuclei of the medium being measured by NMR at least partially realign (longitudinally relax) with the static magnetic field induced by the logging instrument. If the wait time is longer than the longitudinal relaxation time, $T_1$, of a particular component in the formation, the fractional contributions to the spin echo amplitudes of that particular component in subsequent CPMG sequences will be substantially unchanged. Since water in the pore spaces of earth formations typically has a shorter transverse relaxation time, $T_2$, than does oil in earth formations, the longitudinal relaxation time, $T_1$ of the water will also be shorter than that of oil. CPMG sequences can be made using two different values of TW, both of which values of TW are longer than the $T_1$ of water and are therefore long enough to so that no substantial change in the amplitude of the water-generated spin echo signals will occur from one CPMG sequence to the next. One of the TW values, however, should at least be shorter than the $T_1$ of the oil and therefore short enough to have a material effect on the amplitude of the oil-generated spin echo signals. More generally, the TW values should be selected so that there is a substantially different amount of longitudinal relaxation in the oil at one TW than at the other TW. By selecting TW values having these relationships to the $T_1$ values of oil and water, it becomes possible to separate the water contribution to the spin echo amplitudes ("water signal") from the oil contribution to the spin echo amplitudes ("oil signal") relatively easily.

Referring now to FIG. 1, the NMR signal acquisition is shown for the first TW at box 2, and for the second TW at box 4 (both use the same value of interecho time TE shown in FIG. 1 as $TE_1$). Acquiring signals at two TW values enables separation of the water signal from the spin echo amplitudes as suggested in the Akkurt and Prammer reference, for example, by calculating an "echo difference" between time-correspondent spin echoes in the CPMG spin echo amplitude sets made using the two different values of TW. For each individual spin echo time, nTE, in the CPMG sequences made using a single value of interecho spacing, TE, the echo difference amplitude, ECDF, can be described by the following expression:

where $M_0$ represents the amplitude of the spin echoes extrapolated to a time of zero from $$ECDF(nTE) = \sum_l M_{0l}\alpha_{wl}\exp(-nTE/T_{2l}) + \sum_k M_{0k}\alpha_{ok}\exp(-nTE/T_{2k}) \quad (4)$$

the initial transverse radio-frequency polarization (the first 90° RF pulse), and $\alpha_{wl}$ and $\alpha_{ok}$ represent, respectively, the $T_1$ (longitudinal relaxation) partial recovery factors for water and for oil. k and l, respectively, represent the $T_2$ (transverse relaxation) values for each of the transverse relaxation time "bins" generated by the inversion process described in the Miller et al reference or the Prammer et al '115 patent, supra. Partial recovery factors $\alpha_{wl}$ and $\alpha_{ok}$ can be determined by the following expressions:

$$\alpha_{wl} = [\exp(-TW_S/T_{1l}) - \exp(-TW_L/T_{1l})] \quad (5)$$

$$\alpha_{ok} = [\exp(-TW_S/T_{1k}) - \exp(-TW_L/T_{1k})] \quad (6)$$

where $TW_S$ and $TW_L$ represent the shorter and the longer TW values, respectively. $\alpha_{wl}$ and $\alpha_{ok}$ are independent of TE. If $TW_S$ and $TW_L$ are selected as previously explained, (where the $T_1$ of the water is less than both $TW_S$ and $TW_L$), then the water partial recovery factor will be about equal to zero. If the oil partial recovery factor is substantially larger than zero (which will be the case if the TW values are selected as previously explained), then the echo difference, ECDF, will substantially represent only the oil signal. This can be represented by the expression:

$$ECDF(nTE) = \sum_k M_{0k}\alpha_{ok}\exp(-nTE/T_{2k}) \quad (7)$$

Equation (7) can be used to calculate an apparent $T_2$ for the oil, for example by inversion processing the echo difference amplitudes, as will be further explained. Calculating the ECDF data is shown for $TE_1$ at box 8 in FIG. 1.

In the invention, CPMG sequences can be measured for the two different values of TW as previously described. For each value of TW, at least two different CPMG sequences can be measured, each of these at least two sequences having a different value of interecho spacing time, TE. Expressed differently, for each individual TE, two CPMG sequences each having one of the previously described values of TW can be measured. Acquisition of CPMG sequences at the second TE for both TW values is shown at boxes 6 and 18 in FIG. 1. Therefore an echo difference, and consequently and apparent $T_2$ for the oil, can be calculated for each value of TE.

The value of the apparent $T_2$ for the oil, calculated from the echo difference (ECDF) data measured at a first selected value of TE, can be used in combination with the apparent value of $T_2$ for the oil calculated from the echo difference (ECDF) data measured at at least a second, different value of TE, shown at box 12 in FIG. 1, to determine a value for the intrinsic $T_2$ of the oil. Calculating apparent $T_2$ values from ECDF data using each TE value is shown at boxes 10 and 14 in FIG. 1. As was explained in the Background section herein and shown in equation (2), the measured transverse relaxation time $T_2$ includes the effects of the intrinsic relaxation time and self-diffusion. Expressed in terms of amplitude decay rates (R) instead of transverse relaxation times ($T_2$), equation (2) can be rewritten in the form:

$$R_2 = R_{2int} + R_{2D} \quad (8)$$

where the self-diffusion relaxation rate component, $R_2D$, can be determined from the expression:

$$R_{2D} = \frac{\gamma^2 G^2 D\ TE^2}{12} = \frac{\gamma^2 G^2 D\ TE^2}{12} \cdot \frac{1.3 t_k 10^{-5}}{298\eta} \quad (9)$$

The intrinsic relaxation rate, $R_{2int}$, for the oil can be expressed as:

$$R_{2int} \approx \frac{298\eta}{1.2 t_k} \quad (10)$$

The intrinsic relaxation rate can be determined by reducing equations (8) and (9) to a relationship of $R_2$ (the measured relaxation rate for the oil from the ECDF data) with respect to $TE^2$ in the form:

$$R_2 = R_{2int} + C(TE)^2 \quad (11)$$

The value of $R_{2int}$ can be determined for the oil as the value of $R_2$ determined when the relationship in equation (11) is extrapolated to the value of $R_2$ which would obtain at in interecho spacing time of zero (TE=0). This is shown at box 16 in FIG. 1. Using the relationship in equation (10) the viscosity of the oil can be calculated from the value of $R_{2int}$. This is shown in FIG. 1 at box 28.

It should be noted that if the static magnetic field gradient in the location of the NMR excited volume is well known, and the difference in magnetic susceptibility between the solid ("matrix") portion of the earth formation and the fluid filling the pore spaces is also known, the measured relaxation rate $R_2$ can be used to determine the viscosity of the oil by such methods as non-linear least squares fit of the measured relaxation rate to the viscosity and absolute temperature.

In the presence of random noise in the spin echo amplitude signals, it may be desirable to use CPMG echo trains measured at more than two different values of TE in order to reduce the effects of random noise. A suitable method for using more than two TE values to determine the intrinsic transverse relaxation time can be described as follows. First, an echo difference (ECDF) can be calculated for the signals measured at each TE, as previously explained, using the two values of TW. Then, time correspondent amplitudes from each echo difference set can be added together to obtain a single "amplitude sum" value for each TE. Next a ratio of amplitude sums for the shortest TE with respect to the amplitude sums for each of the other TE's can be calculated. For each such ratio, a value of $T_{2int}$ and self-diffusion constant, D, can be calculated. Values for $T_{2int}$ and D can be determined from the ratios. This can be shown by the following expressions relating the shortest TE ($TE_1$) to a second TE ($TE_2$):
Similar expressions can be used to calculate a ratio of amplitude sums for the first and $$R = \frac{\sum ECDF@TE_1}{\sum ECDF@TE_2} \approx \quad (12)$$

$$\frac{\sum \exp(-mTE_2/T_{2int})\exp(-\gamma^2 G^2 DTE_1^2(mTE_2)/12)}{\sum \exp(-mTE_2/T_{2int})\exp(-\gamma^2 G^2 DTE_2^2(mTE_2)/12)}$$

third TE's. The expressions in equation (12) can be used to calculate the diffusion constant and intrinsic transverse relaxation time. Because there are two values to solve, $T_{2int}$ and D, at least two values of ratio R must be determined. It can be inferred from the expressions in equation (12) that at least three values of TE must be used in order to calculate two values of the ratio R. It should be noted that the technique using three TE's described above is equally applicable to using four or more TE's. As more TE's are used, the effect of noise on the results will be progressively reduced. As a practical matter, the number of TE's used will depend on any requirements of logging speed and/or available time to make measurements using multiple TE's.

2. Determining the Longitudinal Relaxation Time

Using the spin echo amplitude signals generated using the two values of TW as previously described, it is also possible to determine the longitudinal relaxation time, $T_1$ of the fluids in the earth formations. The longitudinal relaxation time can also be used to determine the viscosity of the oil in the pore spaces of the earth formations. First, the CPMG sequence acquired with a single TE at the longer value wait time, $TW_L$, can be inverted using, for example, the inversion process described in the Miller et al reference or the Prammer et al '115 patent to provide a $T_2$ distribution. The values of $T_2$ in the $T_2$ distribution which correspond only to values likely to represent the oil signal can be used to generate a first "partial porosity" for the oil, represented by the variable ΣPPORL. This is shown in box 20 in FIG. 1.

An echo difference ECDF for the spin echo amplitudes can then be generated as previously described using the spin echo amplitudes measured at each of the two different values of TW and using the same value of TE. This is shown in box 12 in FIG. 1. The ECDF values can then be used to calculate a second partial porosity for the oil using, for example, the inversion process described in the Miller et al reference or the Prammer et al '115 patent. The second partial porosity can be represented by the variable ΣPPORDF since the second partial porosity is generated from the echo difference amplitudes. This is shown in box 24 in FIG. 1.

If the oil has the approximate NMR response of having only a single $T_1$ value and the long wait time $TW_L$ is more than the $T_1$ of the oil, the oil filled porosity can be approximated by the expression:

$$\Sigma PPORL = \phi_{oil}(1-\exp(-TW_L/T_1)) \approx \phi_{oil} \quad (13)$$

The second (echo difference) partial porosity can be represented by the expression:

$$\Sigma PPORDF = \phi_{oil}(\exp(-TW_S/T_1)-\exp(-TW_L/T_1)) \approx \phi_{oil}\exp(-TW_S/T_1) \quad (14)$$

where the approximation in both equations (13) and (14) is based on the long wait time $TW_L$ being much larger than the longitudinal relaxation time. The expressions in equations (13) and (14) can be rearranged to:

$$\frac{\sum PPORL}{\sum PPORDF} \approx \exp(TW_S/T_1) \quad (15)$$

which can be solved for $T_1$ by the expression:

$$T_1 \approx TW_s \cdot \left(\left[\ln \sum \frac{PPORL}{\sum PPORDF}\right]\right)^{-1} \quad (16)$$

This is shown in box 26 in FIG. 1. It should be noted that the value of the ratio ΣEPPORL/ΣPPORDF is substantially independent of the value of TE used for the CPMG sequences. This makes possible an improvement in the accuracy of determining $T_1$ by making CPMG measurements at more than one TE, using the same values of TW. Specifically, the value of $T_1$ can be estimated by summing each of the values of the ratio ΣEPPORL/ΣPPORDF determined at each value of TE in order to reduce the effect of random noise in the spin echo amplitude measurements. $T_1$ can be calculated using multiple TE's by the expression:

$$T_1 \approx TW_s \cdot \left(\left[\ln \sum_{y=1}^{K} \frac{\sum PPORL(TE_y)}{\sum_{y=1}^{K} \sum PPORDF(TE_y)}\right]\right)^{-1} \quad (17)$$

where y represents the index of the TE value and K represents the total number of TE values.

Multiple TW values can also be used to determine $T_1$ using a technique similar to the one described by equation (17). Equation (17) can be generalized for the case where multiple TW's are used by the expression:

$$T_1 \approx \sum_{m=1}^{M-1} TW_s \left[\sum_{m=1}^{M-1} \ln \sum_{y=1}^{K} \frac{\sum PPORL(TE_y)}{\sum_{y=1}^{K} \sum PPORDF(TE_y)}\right]^{-1} \quad (18)$$

where M represents the total number of TW values, and ranges in index, m, from 1 to M−1 (so as to exclude the longest TW value, $TW_L$). The viscosity of the oil can be calculated form the value of $T_1$ using methods known in the art. A relationship very similar in form to equation (1) in the Background section herein relates longitudinal relaxation time to viscosity. Calculating viscosity is shown in box 28 in FIG. 1.

An alternative method for determining the longitudinal relaxation time can be described as follows. CPMG sequences can be acquired using different values of TW, just as for previous embodiments of the invention. At least two TW values are needed for this method for determining $T_1$, but as will be further explained, the results will be improved by measuring CPMG sequences at three or more values of TW. This is shown in boxes 30, 32 and 34 in FIG. 2. Using an inversion technique such as the one described in the Miller et al reference or the Prammer et al '115 patent, for example, a $T_2$ distribution for each set of spin echo amplitudes can be generated. This is shown in boxes 40, 42 and 44 for CPMG sequences measured using each respective value of TW. The oil signal can be separated from the $T_2$ distributions from each inverted sequence. This can be done empirically by selecting amplitudes in $T_2$ "bins" having values of $T_2$ which are known to exist for the crude oil, or alternatively, can be done by calculating an echo difference, as previously described, between the CPMG sequences measured using the longest TW and the CPMG sequences using any other TW. The echo difference amplitudes can be inverted, using the technique disclosed in the Prammer et al '115 patent or the like, and $T_2$ values of the inverted echo differences which exhibit non-zero amplitudes can be used to determine which $T_2$ values should be used as the "oil signal" from the previously described inverted spin echo amplitudes.

The $T_2$ values which are used as the oil signal should have their amplitudes summed, for each inversion processed CPMG sequence. Such sums can be referred to as the "partial porosity" of the oil ($\Sigma$PPOR) for each value of TW, as shown in boxes 50, 52 and 54. A ratio of the partial porosity calculated using the longest TW with respect to the partial porosity calculated for each of the other (indexed as the y-th) value of TW can be related to the longitudinal relaxation time, $T_1$, of the oil by the expression:

$$R = \frac{\sum PPOR @ TW_L}{\sum PPOR @ TW_s^y} \approx \frac{1}{1 - \exp(-TW_s^y / T_1)} \quad (19)$$

This is shown in boxes 60 and 62. Equation (19) can be solved for $T_1$ as:

$$T_1 = \frac{-TW_s^y}{\ln(1 - R^{-1})} \quad (20)$$

This is shown in box 70. $T_1$ can be determined as the slope of a line defined by equation (20). Using three or more values of TW can improve the accuracy of determining the line for equation (20) and so can improve the accuracy of the results. Results using multiple TE's can also be summed, as explained in the previous embodiment of the invention, to reduce the effects of noise or random error on the results.

The previously described methods for determining the longitudinal relaxation time require that the longer value of TW be greater than the $T_1$ for the oil (or whatever the longest relaxing phase is in the particular earth formation). As a practical matter this condition may not always be met since the longitudinal relaxation time for some crude oils in earth formations can exceed 30 seconds. An alternative method for determining $T_1$ can use a long TW value which is somewhat less than the $T_1$ for oil. This alternative method for determining the longitudinal relaxation time requires acquiring spin echo amplitudes using at least two values of wait time.

Figure 2:
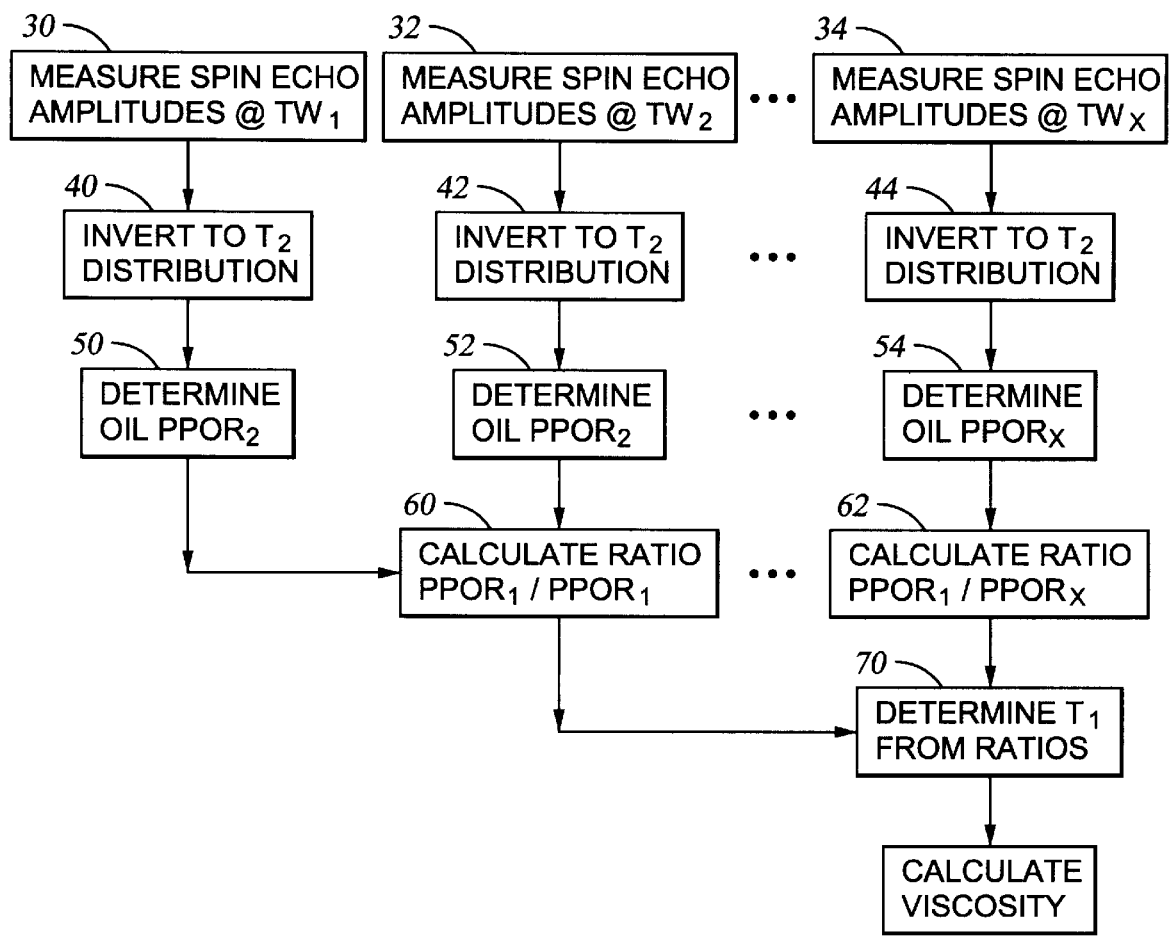
FIG. 2 is a flow chart of an alternative embodiment of the invention.

First, partial porosities for the oil can be calculated from the spin echo amplitudes acquired (30 and 32 in FIG. 2) at each value of TW for a single value of TE. Each of these partial porosities can be calculated by inverting the spin echo amplitudes and selecting and summing the inverted amplitudes from the appropriate $T_2$ bins, as for the previous embodiment of the invention. This is shown in FIG. 2 at 40 and 50 for the long TW, and at 42 and 52 for the short TW. These partial porosities can be represented by $PPOR_1$, and $PPOR_2$ for the long and short TW values, respectively. A ratio of partial porosities can be calculated as for the previous embodiment of the invention, as shown at 60. However, because the long TW value in this embodiment is not longer than the $T_1$ value for the oil, the ratio has a different physical representation, as shown in the following expression:

$$R = \frac{\sum PPOR @ TW_L}{\sum PPOR @ TW_s^y} \approx \frac{1 - \exp(-TW_L / T_1)}{1 - \exp(-TW_s / T_1)} \quad (21)$$
$$= \frac{1 - ([\exp(-TW_L / T_1)])^{(TW_L / TW_s)}}{1 - \exp(-TW_s / T_1)} = \frac{1 - Z^{(TW_L / TW_s)}}{1 - Z}$$

Equation (21) can be rewritten in the form:

$$Z^{(TW_L / TW_s)} - RZ + (R-1) = 0 \quad (22)$$

If the long and short wait times are selected so that their ratio $TW_L / TW_S$ is equal to an integer such as 2 or 3, then analytical solutions for the variable Z can be readily calculated. Finally, the longitudinal relaxation time, $T_1$, can be calculated from Z by the expression:

$$T_1 = \frac{TW_S}{\ln Z} \quad (23)$$

This is shown at 70 in FIG. 2. If the TW values are selected so that their ratio is 2, for example, there will be two solutions for Z, however one of these will have no physical meaning, because the ratio R must have a value of between one and two, for all values of Z between zero and one. This provides a constraint to select the proper solution to algebraic equation (22).

It should be noted that the ratio R is independent of the value of TE, just as for the previous embodiment of the invention. The effects of noise can be reduced by summing ratios, R, determined from the spin echo amplitudes measured at two or more different TE values. This can be shown by the expression:

$$R = \frac{\sum_{l=1}^{k} [\sum PPOR_1 @ TW_L (@ TE_l)]}{\sum_{l=1}^{k} [\sum PPOR_2 @ TW_S (@ TE_l)]} \quad (24)$$

Those skilled in the art will devise other embodiments of the invention which do not depart form the spirit of the invention as disclosed herein. The invention should be limited in scope only by the attached claims.

What is claimed is:

1. A method for determining an intrinsic transverse relaxation time of a first mobile phase in a porous medium having said first phase and a second mobile phase in pore spaces therein using nuclear magnetic resonance spin echo amplitudes measured at first and second interecho spacings, the method comprising:

separating components corresponding to said first phase from said spin echo amplitudes measured at said first interecho spacing;

repeating said step of separating components for said spin echo amplitudes measured at said second interecho spacing;

calculating an apparent transverse relaxation time of said first phase from said separated components for each of said interecho spacings;

determining a relationship of said apparent transverse relaxation time with respect to said interecho spacing; and determining said intrinsic relaxation time from said relationship.

2. The method as defined in claim 1 wherein said intrinsic relaxation time is determined by extrapolating said relationship to an interecho spacing of zero.

3. The method as defined in claim 1 further comprising calculating a viscosity of said first phase from said intrinsic relaxation time.

4. The method as defined in claim 1 further comprising:

acquiring said spin echo amplitudes at at least one additional interecho spacing, repeating said step of separating said components from said amplitudes measured using said at least one additional interecho spacing and determining an apparent transverse relaxation time of said first phase therefrom; and wherein said relationship of said apparent relaxation time with respect to said interecho spacing time comprises determining ratios, each said ratio representing sums of time correspondent echo difference amplitudes for a shortest one of said interecho spacings with respect to echo difference amplitudes from one of the other ones of said interecho spacings, two of said ratio values used to solve for a self-diffusion constant and said intrinsic transverse relaxation time.

5. The method as defined in claim 1 wherein said first phase comprises oil.

6. The method as defined in claim 1 wherein said second phase comprises water.

7. The method as defined in claim 1 wherein said porous medium comprises an earth formation.

8. The method as defined in claim 1 wherein said amplitudes are measured using Carr-Purcell-Meiboom-Gill sequences.

9. The method as defined in claim 1 wherein said step of separating components comprises calculating differences between time correspondent spin echo amplitudes measured at a first wait time and measured at a second wait time, said first wait time providing substantially different longitudinal relaxation of said first phase than said second wait time, said first and second wait times selected to provide substantially complete longitudinal relaxation of said second phase.

10. The method as defined in claim 9 further comprising determining a longitudinal relaxation time of said first phase, comprising:

inverting spin echo amplitudes measured at said first wait time and at a first one of said interecho spacings to obtain a transverse relaxation time distribution;

determining a partial contribution of said first phase from said distribution by measuring magnitudes of relaxation time components corresponding to known values of transverse relaxation times for said first mobile phase;

determining said longitudinal relaxation time by comparing said partial contribution to magnitudes of said separated components from said first interecho spacing.

11. The method as defined in claim 10 further comprising repeating said steps of inverting amplitudes and determining said partial contribution, repeating said step of separating said components, and determining a longitudinal relaxation time using spin echo amplitudes measured at a second one of said interecho spacings, and summing comparisons of said partial contributions with respect to said magnitudes of said separated components to obtain a random error-reduced value of said longitudinal relaxation time.

12. A method for determining a longitudinal relaxation time of a first mobile phase in a porous medium having said first and a second mobile phase in pore spaces therein, using measurements of nuclear magnetic resonance spin echo amplitudes made at a first and a second wait time, said first wait time longer than a longitudinal relaxation time of said first phase, said second wait time shorter than said first wait time, said first and said second wait times longer than a longitudinal relaxation time of said second mobile phase, the method comprising:

determining a first partial contribution of said first phase by inversion processing said spin echo amplitudes measured using said first wait time;

determining a second partial contribution of said first phase by determining differences between said spin echo amplitudes measured using said first and said second wait times, and inversion processing said differences;

determining said longitudinal relaxation time of said first mobile phase by comparing said first partial contribution and said second partial contribution.

13. The method as defined in claim 12 further comprising determining a viscosity of said first phase from said longitudinal relaxation time.

14. The method as defined in claim 12 further comprising summing first and second partial contributions determined from spin echo amplitude measurements made at each one of a plurality of different interecho spacings for each said first and second wait times to reduce effects of random error on calculations of said longitudinal relaxation time.

15. The method as defined in claim 12 further comprising:

measuring spin echo amplitudes using at least one additional wait time, said at least one additional wait time shorter than a longitudinal relaxation time of said first mobile phase and different from said second wait time; and determining said longitudinal relaxation time by summing functions, each said function representing a ratio of said first partial contribution to a partial contribution calculated by inverting differences between spin echo amplitudes measured using said first wait time and spin echo amplitudes measured using one of said second and said at least one additional wait time.

16. The method as defined in claim 15 further comprising determining viscosity of said first mobile phase from said longitudinal relaxation time.

17. A method for determining a longitudinal relaxation time of a first mobile phase in a porous medium having said first and a second mobile phase in pore spaces therein, using nuclear magnetic resonance spin echo amplitudes measured at first and second wait times, said first wait time longer than said longitudinal relaxation time of said first phase, said second wait time shorter than said first wait time, said first and second wait times providing substantially complete longitudinal relaxation of said second phase, the method comprising:

determining a first partial contribution of said first phase from said spin echo amplitudes measured at said first wait time;

determining a second partial contribution of said first phase from said spin echo amplitudes measured at said second wait; and calculating said longitudinal relaxation time from a first ratio of said first and said second partial contributions.

18. The method as defined in claim 17 further comprising calculating a viscosity of said first phase from said longitudinal relaxation time.

19. The method as defined in claim 17 wherein said first phase comprises oil.

20. The method as defined in claim 17 wherein said second phase comprises water.

21. The method as defined in claim 17 wherein said porous medium comprises an earth formation.

22. The method as defined in claim 17 wherein said first and said second partial contributions are determined by inverting said spin echo amplitudes measured at corresponding wait times, and selecting transverse relaxation times of said inverted amplitudes corresponding to transverse relaxation times of said first phase, said corresponding transverse relaxation times determined by inverting differences between said spin echo amplitudes measured at said first and said second wait times, and determining transverse relaxation times for which said inverted differences are non-zero.

23. The method as defined in claim 17 further comprising:

determining a third partial contribution of said first phase by inverting spin echo amplitudes measured at a third wait time, said third wait time shorter than said first wait time and different from said second wait time;

calculating a second ratio of said first partial contribution with respect to said third partial contribution; and determining said longitudinal relaxation time from said first and said second ratios.

24. The method as defined in claim 23 wherein said longitudinal relaxation time corresponds to a slope of a linear relationship between said second and third wait times and a logarithm of said first and said second ratios.

25. A method for determining a longitudinal relaxation time of a first mobile phase in a porous medium having said first and a second mobile phase in pore spaces therein using nuclear magnetic resonance spin echo amplitudes measured at first and second wait times, said first wait time longer than said second wait time, said first and second wait times each providing a substantially different longitudinal relaxation than the other wait time, said first and second wait times selected to provide substantially complete longitudinal relaxation of said second phase, said first and said second wait times selected to provide an analytical solution to an algebraic equation, the method comprising:

determining a first partial contribution of said first phase;

determining a second partial contribution of said first phase; and calculating said longitudinal relaxation time from a first ratio of said first and said second partial contributions.

26. The method as defined in claim 25 wherein said first and said second partial contributions are determined by inverting said spin echo amplitudes measured at corresponding wait times, and selecting transverse relaxation times of said inverted amplitudes corresponding to transverse relaxation times of said first phase, said corresponding transverse relaxation times determined by inverting differences between said spin echo amplitudes measured at said first and said second wait times, and determining transverse relaxation times for which said inverted differences are non-zero.

27. The method as defined in claim 25 further comprising calculating a viscosity of said first phase from said longitudinal relaxation time.

28. The method as defined in claim 25 wherein said first phase comprises oil.

29. The method as defined in claim 25 wherein said second phase comprises water.

30. The method as defined in claim 25 wherein said porous medium comprises an earth formation.

31. The method as defined in claim 25 wherein said first wait time is twice said second wait time.

32. The method as defined in claim 25 further comprising calculating first and second partial contributions from spin echo amplitudes measured using a different value of interecho spacing, calculating a second ratio of said partial contributions at said different interecho spacing and summing said first and said second ratios to determine said longitudinal relaxation time.

* * * * *